(12) United States Patent
Trieu et al.

(10) Patent No.: US 11,565,060 B2
(45) Date of Patent: Jan. 31, 2023

(54) EVAPORATOR UNIT FOR AN INHALER HAVING A WICK STRUCTURE WITH MICROCHANNELS

(71) Applicant: KÖRBER TECHNOLOGIES GMBH, Hamburg (DE)

(72) Inventors: Hoc Khiem Trieu, Westergellersen (DE); Karen Kalaydzhyan, Hamburg (DE); Sven Bohne, Hamburg (DE)

(73) Assignee: KÖRBER TECHNOLOGIES GMBH, Hamburg (DE)

( * ) Notice: Subject to any disclaimer, the term of this patent is extended or adjusted under 35 U.S.C. 154(b) by 345 days.

(21) Appl. No.: 16/755,697

(22) PCT Filed: Oct. 11, 2018

(86) PCT No.: PCT/EP2018/077737
§ 371 (c)(1),
(2) Date: Apr. 13, 2020

(87) PCT Pub. No.: WO2019/072969
PCT Pub. Date: Apr. 18, 2019

(65) Prior Publication Data
US 2021/0195952 A1    Jul. 1, 2021

(30) Foreign Application Priority Data

Oct. 13, 2017  (DE) .......................... 102017123868.9

(51) Int. Cl.
*A24F 13/00*    (2006.01)
*A24F 17/00*    (2006.01)
(Continued)

(52) U.S. Cl.
CPC ............. *A61M 15/06* (2013.01); *A24F 40/44* (2020.01); *A24F 40/46* (2020.01); *A24F 40/48* (2020.01); *H05B 3/42* (2013.01); *A24F 40/10* (2020.01)

(58) Field of Classification Search
CPC .......... A24F 40/10; A24F 40/44; A24F 40/46; A24F 40/48; A61M 11/042;
(Continued)

(56) References Cited

U.S. PATENT DOCUMENTS 10,543,323 B2 *   1/2020  Buchberger ............ A24F 40/44
11,272,739 B2 *   3/2022  Schmidt ............... A61M 11/042
(Continued)

FOREIGN PATENT DOCUMENTS

AT        507 187 A4      10/2008
CN        105661649       6/2016
(Continued)

OTHER PUBLICATIONS

1st Examination Report issued by the German Patent and Trademark Office with respect to the priority German Patent Application No. 10 2017 123 868.9.
(Continued)

*Primary Examiner* — Abdullah A Riyami
*Assistant Examiner* — Thang H Nguyen
(74) *Attorney, Agent, or Firm* — Saliwanchik, Lloyd & Eisenschenk (57) ABSTRACT

An evaporator unit for an inhaler, in particular for an electronic cigarette product, comprises an electrically operable, in particular planar, heating body which has an inlet side and an outlet side, and a plurality of microchannels which each extend from the inlet side to the outlet side through the heating body, the heating body being designed to evaporate, by applying a heating voltage, liquid trans-
(Continued)

ferred through the microchannels. A porous and/or capillary wick structure is arranged on the inlet side of the heating body, which structure rests flat against and in contact with the heating body and covers all of the microchannels on the inlet side.

27 Claims, 5 Drawing Sheets

(51) Int. Cl.
*A24F 25/00* (2006.01)
*A61M 15/06* (2006.01)
*A24F 40/44* (2020.01)
*A24F 40/46* (2020.01)
*A24F 40/48* (2020.01)
*H05B 3/42* (2006.01)
*A24F 40/10* (2020.01)

(58) Field of Classification Search
CPC ............... A61M 15/025; A61M 15/06; A61M 2016/0021; A61M 2205/3317; A61M 2205/50; A61M 2205/8206; B05B 7/1686; H05B 3/42
See application file for complete search history.

(56) References Cited

U.S. PATENT DOCUMENTS

| | | |
|---|---|---|
| 2011/0226236 A1 | 9/2011 | Buchberger |
| 2013/0056012 A1 | 3/2013 | Hearn et al. |
| 2015/0059780 A1 | 3/2015 | Davis |
| 2016/0338410 A1* | 11/2016 | Batista .................. F22B 1/284 |
| 2017/0106113 A1* | 4/2017 | Meinhart ................ A61L 9/037 |
| 2017/0178884 A1* | 6/2017 | Murtazin ............ H01J 49/0454 |
| 2018/0249763 A1 | 9/2018 | Schmidt |
| 2019/0133186 A1* | 5/2019 | Fraser .................... A24F 40/46 |
| 2021/0186097 A1 | 6/2021 | Schmidt et al. |

FOREIGN PATENT DOCUMENTS

| | | |
|---|---|---|
| EP | 3 117 860 A1 | 10/2009 |
| EP | 3 372 096 A1 | 3/2018 |
| JP | 2012506263 | 3/2012 |
| JP | 2013520982 | 6/2013 |
| WO | WO 2018/083007 A1 | 5/2018 |
| WO | WO-2022023453 A1 * | 2/2022 |

OTHER PUBLICATIONS

Communication received from the U.S. Patent Office dated Jul. 14, 2021 regarding a Third Party Submission submitted to the U.S. Patent Office on Jul. 9, 2021.
Third-Party Submission under 37 CFR 1.290 and concise description of relevance.

* cited by examiner

EVAPORATOR UNIT FOR AN INHALER HAVING A WICK STRUCTURE WITH MICROCHANNELS

CROSS REFERENCE TO RELATED APPLICATIONS

This application is a National Stage Application of International Application Number PCT/EP2018/077737, filed Oct. 11, 2018; which claims priority to German Patent Application No. 102017123 868.9, filed Oct. 13, 2017.

FIELD OF THE INVENTION

The present invention relates to an evaporator unit for an inhaler, in particular for an electronic cigarette product, comprising an electrically operable, in particular planar, heating body which has an inlet side and an outlet side, and a plurality of microchannels which each extend from the inlet side to the outlet side through the heating body, the heating body being designed to evaporate, by applying a heating voltage, liquid transferred through the microchannels.

BACKGROUND

In the prior art, the liquid is typically supplied to the heating body in a capillary manner by means of a wick. The wicks used ideally have a constant transfer effect in the transfer direction. If the transfer rate is lower than the required evaporation rate, the wick dries out in close proximity to the heating body. A dry puff follows and harmful substances are released.

In the case of a planar heating body, the heating body must be wetted as uniformly as possible by the wick at all times and in every location in order to ensure a constant temperature distribution and thus uniform, pollutant-free evaporation over the surface thereof.

In the current prior art, Si-based heaters for e-cigarettes are proposed. None of these systems have been implemented so far. There is a particular difficulty in the electrical, mechanical and hydraulic coupling of the heaters with simultaneous thermal decoupling of the structure and the avoidance of transition losses.

BRIEF SUMMARY

The problem addressed by the invention is that of providing an evaporator unit in which problems due to bubble formation and dry running on the inlet side of the heating body are avoided.

The invention solves this problem by means of the features of the independent claims.

The formation of bubbles in the inlet region of the heating body can be counteracted by means of the wick structure according to the invention. Bubbles that form in the microchannels of the heating body cannot penetrate into the region upstream of the inlet side, and lead to dry running of the inlet region of the heating body and thus to a functional impairment of the evaporator. Any bubbles in the region of the wick structure are trapped in the pores or capillaries thereof and cannot form large bubbles. It is important that the wick structure rests flat against and in contact with the heating body on the inlet side and covers all of the microchannels on the inlet side such that individual bubbles that form in the microchannels cannot leave the microchannels in the wrong direction, specifically on the inlet side towards the liquid store device. Instead, the blockage of the inlet side by the wick structure according to the invention ensures that bubbles formed in the microchannels migrate in the microchannels towards the outlet side, where they are expelled from the microchannels and can then no longer cause problems.

So that the part of the wick structure on the inlet side of the heating body is uniformly supplied with liquid, it is advantageous to transport the liquid there more slowly and uniformly than in the region of the wick structure which is more distant from the heating body and closer to the liquid store. Consequently, the wick regions advantageously have a pore/capillary size gradient from large to small in the direction towards the heating body. As a result, the transfer rate advantageously decreases along the wick structure in the direction towards the heating body. At a constant surface tension and viscosity of the liquid, the transfer rate of the wick structure depends solely on the hydrophobicity and the pore/capillary size of the wick material.

The average size of the pores or capillaries in the porous or capillary material of the wick structure is advantageously subject to specific requirements. Thus, the average pore/capillary size of pores or capillaries in the wick structure in the contact region with the heating body is advantageously minimal, and particularly advantageously smaller, preferably at least one order of magnitude smaller, than the smallest distance of two microchannels from one another. In this way, bubbles formed in a microchannel on the inlet side of the heating body are advantageously prevented from being able to pass or penetrate into a bordering microchannel. In other words, the described feature prevents individual microchannels from communicating with one another via the liquid in the inlet region. Otherwise, a stable evaporation state of individual microchannels could not result due to interacting microchannels. In addition, large vapour bubbles formed in the wick structure on the inlet side of the heating body can block a plurality of microchannels at the inlet openings thereof at the same time, which could cause them to overheat.

The average pore/capillary size of pores or capillaries in the wick structure in the contact region with the heating body is also advantageously smaller, preferably at least one order of magnitude smaller, than the smallest inside (or hydraulic) diameter of the microchannels. In this way, bubbles formed in the microchannels are effectively prevented from being able to undesirably penetrate through the pores or capillaries into the interior of the wick structure. Furthermore, the maximum possible bubble size inside the wick structure is advantageously limited to the pore or capillary size.

In a particularly advantageous embodiment, the average pore/capillary size is not constant over the wick structure, but changes, in particular reduces (preferably monotonically) as the distance from the heating body decreases. A monotonic decrease in the pore/capillary size generally implies that the pore/capillary size remains the same in portions, but in any case does not increase as the distance from the heating body decreases.

The liquid is transported from the wick structure into the microchannels by heating the liquid below the heating body, by the resulting lowering of the surface tension of the liquid and furthermore by the thus increased capillary forces. The liquid evaporating in the heating body leads to a pressure difference and to a change in concentration with a gradient towards the outlet side of the heating body. The pressure difference increases the capillary pressure within the individual microchannels and likewise means that the evaporating liquid can only evaporate away from the wick structure without influencing bordering microchannels.

Average pore/capillary size here means averaged over a plurality of corresponding pores or capillaries. Average pore size means average value over the diameter of spheres which each have the same volume as the corresponding pores. Average capillary size means average value over the diameter of cylinders which each have the same length and the same volume as the corresponding capillaries.

The previously described wick structure can be advantageously implemented in several ways. In an advantageous embodiment, the wick structure can be constructed in a discrete or multi-stage manner and have a plurality of porous and/or capillary layers resting one on the other and each having a constant average pore/capillary size. This embodiment can be particularly easy to produce in terms of manufacturing.

In an alternative embodiment, the wick structure can be constructed as an element having a gradual change in the average pore/capillary size as a function of the distance from the heating body. In this variant there is therefore only one layer having a gradual and monotonic change, in particular a decrease in the pore/capillary size in the direction towards the heating body. This has the advantage of a reduced number of parts.

Mixed forms of the previously described embodiments are possible. For example, a layer having a constant, small average pore/capillary size can be provided in the region of the inlet side of the heating body and resting thereagainst, towards the liquid store, is a layer having a steadily or continuously increasing average pore/capillary size.

The transfer rate of the wick structure is advantageously at least as great as the maximum evaporation rate of the heating body. This ensures adequate liquid tracking at all times such that disadvantageous dry-running of the heating body is prevented. The evaporation rate is determined by the geometry of the heating body structure (volume vs. surface) and the evaporator output.

Accordingly, the capillary wick structure is designed to transfer the liquid uniformly over the entire volume thereof to the heating body. The transfer rate of the wick structure and the evaporation rate of the heating body are set in relation to one another such that the transfer rate can manage at least the rate of evaporation. This prevents too little liquid from being present on the heating body during the evaporation process, as a result of which said heating body would dry out.

The wick structure can advantageously consist wholly or partially of cotton, cellulose, acetate, glass fibre fabric, glass fibre ceramic, sintered ceramic, ceramic paper, aluminosilicate paper, metal foam, metal sponge, another heat-resistant, porous and/or capillary material having a suitable transfer rate, and/or a combination of two or more of the aforementioned materials.

The frequency and/or duty cycle of a heating voltage Uh for the heating body are preferably adapted to the natural vibration and/or natural frequency of vibrations of gas bubbles formed in the microchannels. This is based on the knowledge that evaporation with passive capillary liquid supply, as in the case of the invention by means of the wick structure, is subject to different laws than evaporation with active supply of the liquid. In order to optimise the evaporation in the sense of uniform, pollutant-free vapour generation, which depends, among other things, on the transfer rate of the liquid to the heating body, the heating voltage for the heating body is advantageously activated in a pulsed manner such that the transfer rate is adapted to the natural vibration of the bubble formation during the bubble boiling in the microchannels.

The frequency and/or the duty cycle of the heating voltage Uh is preferably selected optimally depending on the mixing ratio of the liquid to be evaporated, since the natural frequencies of the bubble vibrations of the liquids and mixtures in question can vary.

However, it has been demonstrated that a preferred heating frequency in the range between 20 Hz and 200 Hz, preferably in the range between 25 Hz and 100 Hz, even more preferably in the range between 30 Hz and 70 Hz and, for example, 50 Hz covers a large part of the liquids and mixtures in question.

The maximum heating current generated for the heating body by the heating voltage Uh is also preferably not more than 7 A in order to ensure concentrated vapour while avoiding overheating.

At least one preload-generating clamping element is preferably provided, which is arranged and designed to clamp the heating body onto the support. The heating body is clamped onto the support by means of the clamping element and is thus held securely and immovably in the evaporator unit.

In a particularly preferred embodiment, the at least one clamping element is simultaneously used as an electrode for electrically contacting and supplying power to the heating body. In this case, separate electrodes for the electrical contacting of the heating body are unnecessary.

At least two clamping elements are preferably provided on opposite sides of the heating body, which facilitates particularly high mechanical stability with relatively little complexity. In a preferred embodiment, the at least one clamping element has a clamping bracket which makes linear contact with the heating body. Due to the line contacting between the clamping bracket and the heating body, there is an excellent electrical connection between the clamping element and the heating body, while at the same time having ideal thermal decoupling between the clamping element and the heating body due to the lack of face-to-face contact.

The clamping element can clamp the heating body laterally to and in parallel with the outlet side and/or vertically onto the outlet side and/or in a corner groove of the support. The latter option involves two contact lines between the clamping bracket and the heating body, which further improves the electrical contacting considerably. A clamping element can also have more than one clamping bracket, in particular any two or all three clamping brackets of the aforementioned type.

In an advantageous embodiment, at least one electrical conductor, which extends through a hole in the support, can be provided for electrically contacting the clamping element and in particular contacts a printed circuit board which is arranged on the side of the support facing away from the heating body. However, it is also advantageously possible for the support itself to be in the form of a printed circuit board, which reduces the number of parts and thus the production complexity.

Accordingly, an advantageous evaporator unit is proposed, in which an in particular planar heating body is clamped linearly, for example on two opposite sides, and is thereby simultaneously electrically contacted. Due to the resilient clamping, a contact pressure is exerted on the wick material under the heater, which balances the evaporation pressure. The wick structure is held in a through-opening in a support and the liquid store is attached under the support.

The clamping is carried out in such a way that air pockets between the heating body and the wick are avoided.

The in particular planar, mechanically stable structure of the heating body favours the uniform surface pressure on the wick structure located underneath said body and thus a uniform supply of liquid. The wick structure advantageously ends raised above the support. As a result, the heating body lying on top has no further mechanical contact with the surroundings and no thermal bridges occur.

The electrical contact is designed such that the maximum required heating current can be transmitted with the minimum possible contact face. The linear contact is formed uniformly over the respective sides of the heating body such that there are no unnecessary transition losses due to inaccurate contacting, which lead to irregular heating in the peripheral regions of the heating body. The metal-silicon contacting also avoids Schottky diode effects by forming a eutectic such that the charge carrier transport advantageously follows Ohm's law.

BRIEF DESCRIPTION OF DRAWINGS

The invention will be explained below on the basis of the preferred embodiments with reference to the accompanying drawings, in which.

DETAILED DESCRIPTION

Figure 1:
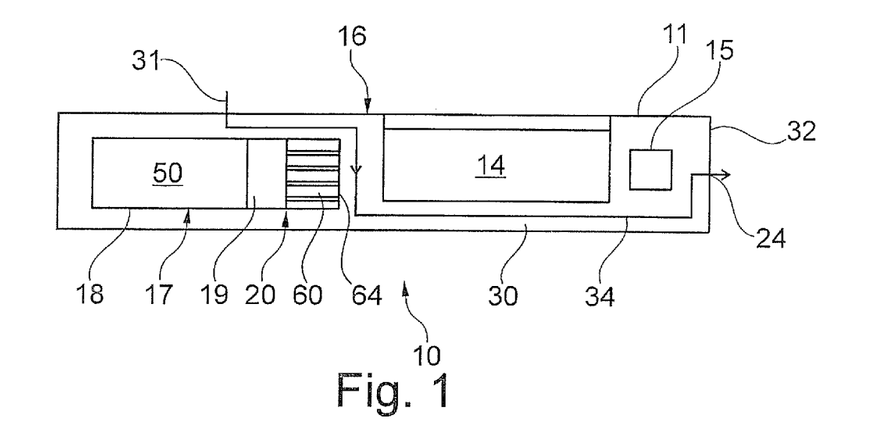
FIG. 1 is a schematic representation of an electronic cigarette product.

The inhaler 10 (e.g., an electronic cigarette product) comprises a housing 11 in which an air channel 30 is provided between at least one air inlet opening 31 and one air outlet opening 24 at a mouth end 32 of the inhaler 10. The mouth end 32 of the inhaler 10 denotes the end at which the consumer puffs for the purpose of inhalation and thereby applies a negative pressure to the inhaler 10 and generates an air flow 34 in the air channel 30.

The inhaler 10 advantageously consists of a base part 16 and a consumption unit or cartridge 17, which comprises the evaporator unit 20 and the liquid store 18 and is in particular in the form of an exchangeable cartridge. The air sucked in through the air inlet opening 31 is conducted in the air channel 30 to or along at least one evaporator unit 20. The evaporator unit 20 is connected or connectable to at least one liquid store 18 in which at least one liquid 50 is stored. The evaporator unit 20 evaporates liquid 50, which is supplied thereto from the liquid store 18, and adds the evaporated liquid as aerosol/vapour 22 (see FIG. 7) into the air flow 34 at an outlet side 64. An advantageous volume of the liquid store 18 is in the range between 0.1 ml and 5 ml, preferably between 0.5 ml and 3 ml, more preferably between 0.7 ml and 2 ml or 1.5 ml.

The inhaler 10 also comprises an electrical energy store 14 and an electronic control device 15. The energy store 14 is usually arranged in the base part 16 and can be, in particular, a disposable electrochemical battery or a rechargeable electrochemical battery, for example a lithium-ion battery. The electronic control device 15 comprises at least one digital data processing device, in particular a microprocessor and/or microcontroller, in the base part 16 (as shown in FIG. 1) and/or in the consumption unit or cartridge 17.

A sensor, such as a pressure sensor or a pressure switch or flow switch, is advantageously arranged in the housing 11, it being possible for the electronic control device 15 to detect, on the basis of a sensor signal output from the sensor, that a consumer is puffing the inhaler 10 at the mouth end 32 in order to inhale. In this case, the electronic control device 15 controls the evaporator unit 20 in order to add liquid 50 from the liquid store 18 as aerosol/vapour into the air flow 34.

The liquid 50 to be dosed that is stored in the liquid store 18 is, for example, a mixture of 1,2-propylene glycol, glycerol, water, at least one flavour and/or at least one active substance, in particular nicotine.

The consumption unit or cartridge 17 advantageously comprises a non-volatile data store for storing information or parameters relating to the consumption unit or cartridge 17. The data store can be part of the electronic control device 15. The data store is advantageously used to store information regarding the composition of the liquid stored in the liquid store 18, information regarding the process profile, in particular power/temperature control; data for state monitoring or system testing, for example seal testing; data regarding copy protection and counterfeit protection, an ID for unique identification of the consumption unit or cartridge 17, serial number, date of manufacture and/or expiry date, and/or puff count (number of inhalation puffs by the consumer) or the period of use. The data store is advantageously connected or connectable to the electronic control device 15 via contacts and/or lines.

Figure 2:
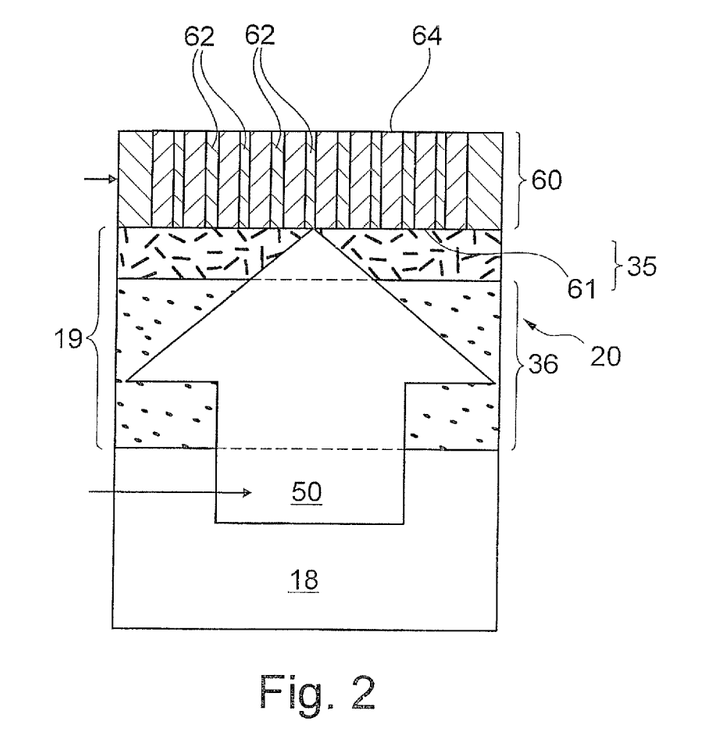
FIG. 2 is a schematic cross-sectional view of an evaporator unit according to the invention.

An advantageous embodiment of an evaporator unit 20 according to the invention is shown in FIG. 2. The evaporator unit 20 comprises a block-shaped, preferably monolithic heating body 60, preferably made of an electrically conductive material, preferably silicon, doped ceramic, metal ceramic, filter ceramic, semiconductor, in particular germanium, graphite, semimetal and/or metal. It is not necessary for the entire heating body 60 to be made of an electrically conductive material. For example, it may be sufficient for the surface of the heating body 60 to be coated in an electrically conductive manner, for example coated with metal. In this case, the entire surface does not have to be coated; for example, conductor tracks can be provided on a non-conductive main body. It is also not absolutely necessary for the entire heating body 60 to heat; it may be sufficient, for example, if a portion or a heating layer of the heating body 60 heats in the region of the outlet side 64.

The heating body 60 is provided with a plurality of microchannels 62 which connect an inlet side 61 of the heating body 60 to an outlet side 64 in a liquid-conducting manner. The inlet side 61 is connected to the liquid store 18 in a liquid-conducting manner via a wick structure 19. The wick structure 19 is used for the passive transfer of liquid from a liquid store 18 to the heating body 60 by means of capillary forces.

The average diameter of the microchannels 62 is preferably in the range between 5 µm and 200 µm, more preferably in the range between 30 µm and 150 µm, even more preferably in the range between 50 µm and 100 µm. Due to these dimensions, a capillary action is advantageously generated such that liquid penetrating into a microchannel 62 on the inlet side 61 rises upwards through the microchannel 62 until the microchannel 62 is filled with liquid. The volume ratio of microchannels 62 to heating body 60, which can be referred to as the porosity of the heating body 60, is, for example, in the range between 10% and 50%, advantageously in the range between 15% and 40%, even more advantageously in the range between 20% and 30%, and is for example 25%. The edge lengths of the faces of the heating body 60 provided with microchannels 62 are, for example, in the range between 0.5 mm and 3 mm. The dimensions of the faces of the heating body 60 provided with microchannels 62 can be, for example: 0.95 mm×1.75 mm or 1.9 mm×1.75 mm or 1.9 mm×0.75 mm. The edge lengths of the heating body 60 can be, for example, in the range between 0.5 mm and 5 mm, preferably in the range between 0.75 mm and 4 mm, more preferably in the range between 1 mm and 3 mm. The face of the heating body 60 (chip size) can be, for example, 1 mm×3 mm or 2 mm×3 mm. The width b of the heating body 60 (see FIG. 10) is preferably in the range between 1 mm and 5 mm, more preferably in the range between 2 mm and 4 mm, and is, for example, 3 mm. The height h of the heating body 60 (see FIG. 10) is preferably in the range between 0.05 mm and 1 mm, more preferably in the range between 0.1 mm and 0.75 mm, even more preferably in the range between 0.2 mm and 0.5 mm and is, for example, 0.3 mm.

The number of microchannels 62 is preferably in the range between four and 1000. This allows the heat input from the substrate into the microchannels 62 to be optimised, ensures a high evaporation capacity and produces a sufficiently large vapour outlet face.

Figure 3:
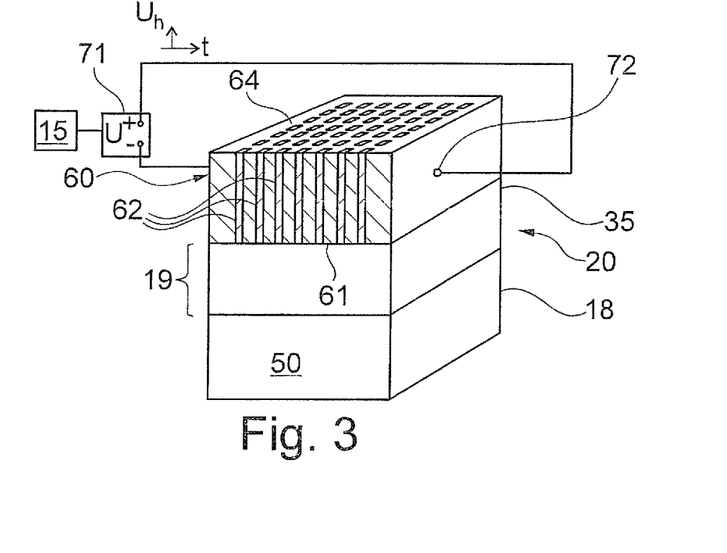
FIG. 3 is a perspective cross-sectional view of an evaporator unit according to the invention.

The microchannels 62 are arranged in the form of a square, rectangular, polygonal, round, oval or differently shaped array, as can be seen in FIG. 3. The array can be in the form of a matrix having s columns and z rows, where s is advantageously in the range between 2 and 50 and more advantageously in the range between 3 and 30 and/or z is advantageously in the range between 2 and 50 and more advantageously in the range between 3 and 30. This allows for an effective and easily manufactured arrangement of microchannels 62 having an ensured high evaporation capacity.

The cross section of the microchannels 62 can be square, rectangular, polygonal, round, oval or otherwise shaped and/or can vary lengthwise in portions, in particular can increase, decrease or remain constant.

The length of one or each microchannel 62 is preferably in the range between 100 µm and 1000 µm, more preferably in the range between 150 µm and 750 µm, even more preferably in the range between 180 µm and 400 µm, and is, for example, 300 µm. In this way, optimal liquid absorption and portion formation with sufficiently good heat input from the heating body 60 into the microchannels 62 can be produced.

The distance of two microchannels 62 from one another is preferably at least 1.3 times the inside diameter of a microchannel 62, the distance being relative to the central axes of the two microchannels 62. The distance can preferably be 1.5 to 5 times, more preferably 2 to 4 times the inside diameter of a microchannel 62. In this way, optimal heat input from the substrate into the microchannels and a sufficiently stable arrangement and wall thickness of the microchannels can be produced.

Due to the features described above, the heating body 60 can also be described as a volume heater.

The evaporator unit 20 has a heating voltage source 71 which is preferably controllable by the electronic control device 15 and is connected via electrodes 72 to opposite sides of the heating body 60 such that an electrical voltage Uh generated by the heating voltage source 71 leads to a current flow through the heating body 60. Due to the ohmic resistance of the electrically conductive heating body 60, the current flow leads to heating of the heating body 60 and therefore to evaporation of the liquid contained in the microchannels 62. The heating body 60 thus acts as an evaporator. The vapour/aerosol generated in this manner escapes to the outlet side 64 from the microchannels 62 and is added to the air flow 34, see FIG. 1. More precisely, upon detection of an air flow 34, caused by the consumer puffing, through the air channel 30, the electronic control device 15 activates the heating voltage source 71, the liquid in the microchannels 62 being driven out of the microchannels 62 in the form of vapour/aerosol by spontaneous heating.

In this case, the duration of the individual evaporation steps at different temperatures and/or an evaporation of the individual components of the individual portions of the liquid can be kept short and/or can be clocked at an activation frequency such that the step-by-step evaporation cannot be perceived by a consumer and nevertheless a largely homogeneous, repeatably precise aerosol formation having good taste conformity can be ensured. In particular, it is advantageous to first evaporate a low-boiling component of the liquid in a first evaporation interval at a first temperature A, and then to evaporate a high-boiling component of the liquid in a second evaporation interval at a second temperature B, which exceeds temperature A.

A voltage curve Uh(t) adapted to the liquid mixture used is preferably stored in the data store of the inhaler 10. This makes it possible to preset the voltage curve Uh(t) so as to be adapted to the liquid used, such that the heating temperature of the heating body 60, and therefore also the temperature of the capillary microchannels 62, can be controlled in accordance with the known evaporation kinetics of the particular liquid over time during the evaporation procedure, as a result of which optimal evaporation results can be achieved. The evaporation temperature is preferably in the range between 100° C. and 400° C., more preferably between 150° C. and 350° C., even more preferably between 190° C. and 290° C.

A porous and/or capillary, liquid-conducting wick structure 19 is arranged on the inlet side 61 of the heating body 60. The wick structure 19 contacts the inlet side 61 of the heating body 60 over the surface and covers all microchannels 62 on the inlet side, as can be seen in FIGS. 2 and 3. On the side opposite the heating body 60, the wick structure is connected to the liquid store in a liquid-conducting manner. The direct attachment of the liquid store 18 to the wick structure 19 shown in FIGS. 1 to 3 and 7 is to be understood only as an example. In particular, a liquid interface and/or a plurality of liquid lines can be provided between the liquid store 18 and the wick structure 19. The liquid store 18 can therefore also be arranged at a distance from the wick structure 19. The dimensions of the liquid store 18 can be greater than the wick structure 19, see for example FIG. 7. The wick structure 19 can, for example, be inserted into an opening in a housing of the liquid store 18. A plurality of evaporator units 20 can also be associated with a liquid store 18.

The wick structure 19 consists of porous and/or capillary material which, due to capillary forces, is able to passively subsequently transfer sufficient liquid evaporated from the heating body 60 from the liquid store 18 to the heating body 60 in order to prevent the microchannels 62 from running dry and to prevent problems resulting therefrom.

The wick structure 19 advantageously consists of a non-conductive material in order to avoid undesired heating of the liquid in the wick structure 19 by means of current flow. The wick structure 19 advantageously consists of one or more of the materials cotton, cellulose, acetate, glass fibre fabric, glass fibre ceramic, sintered ceramic, ceramic paper, aluminosilicate paper, metal foam, metal sponge, another heat-resistant, porous and/or capillary material having a suitable transfer rate, or a combination of two or more of the materials mentioned above. In an advantageous practical embodiment, the wick structure 19 can comprise at least one ceramic fibre paper and/or a porous ceramic. The volume of the wick structure 19 is preferably in the range between 1 mm$^3$ and 10 mm$^3$, more preferably in the range between 2 mm$^3$ and 8 mm$^3$, even more preferably in the range between 3 mm$^3$ and 7 mm$^3$ and is, for example, 5 mm$^3$.

If the wick structure 19 consists of a conductive material, which is not excluded, an insulating layer made of an electrically and/or thermally insulating material, for example glass, ceramic or plastics material, is advantageously provided, between the wick structure 19 and the heating body 60, having through-openings extending through the insulating layer and corresponding to the microchannels 62.

The size of the pores or capillaries in the material of the wick structure 19 is advantageously subject to specific requirements. The average pore/capillary size Dw of pores or capillaries of the wick structure 19 in the contact region and/or the inlet side 61 with the heating body 60 is advantageously minimal, i.e. Dw=Pmin (see FIGS. 5 and 6), and/or advantageously smaller, preferably by at least a factor of 2, more preferably by at least a factor of 5, than the smallest distance Dp of two microchannels 62 from one another, i.e. Dw<<Dp, see FIG. 4. Furthermore, the average pore/capillary size Dw of pores or capillaries of the wick structure 19 in the contact region and/or the inlet side 61 with the heating body 60 is advantageously smaller, preferably by at least a factor of 2, more preferably by at least a factor of 5, than the smallest inside diameter Dpw of a microchannel 62, i.e. Dw<<Dpw. The contact region can be, for example, a wick layer 35.

The wick structure 19 in the contact region and/or the inlet side 61 with the heating body 60 is used to uniformly distribute liquid, to be temperature-resistant and to form a kind of check valve with the relatively small pores and/or thin capillaries thereof in order to prevent undesired backflow of bubble-containing liquid from the heating body 60 into the wick structure 19 and/or into the liquid store 18.

In the embodiment according to FIG. 2, the wick structure 19 has two, for example planar, layers 35, 36, specifically a wick layer 35 which rests flat against and in contact with the inlet side 61 of the heating body 60 and can be referred to as a contact layer, and an adjacent wick layer 36, which is connected to the liquid store 18 in a liquid-conducting manner and can be referred to as a more distant wick layer.

The wick layer 35 has a substantially constant pore/capillary size distribution and a substantially constant average pore/capillary size Dw, which is significantly smaller than the smallest distance Dp of two microchannels 62 from one another and significantly smaller than the smallest inside diameter Dpw of a microchannel 62: Dw<<Dp, Dpw.

The more distant wick layer 36 has a substantially constant pore/capillary size distribution and a substantially constant average pore/capillary size Dw', which is significantly greater than the average pore/capillary size Dw of the wick layer 35: Dw'>Dw, but still preferably less than Dp and/or Dpw: Dw'<Dp, Dpw.

Figure 4:
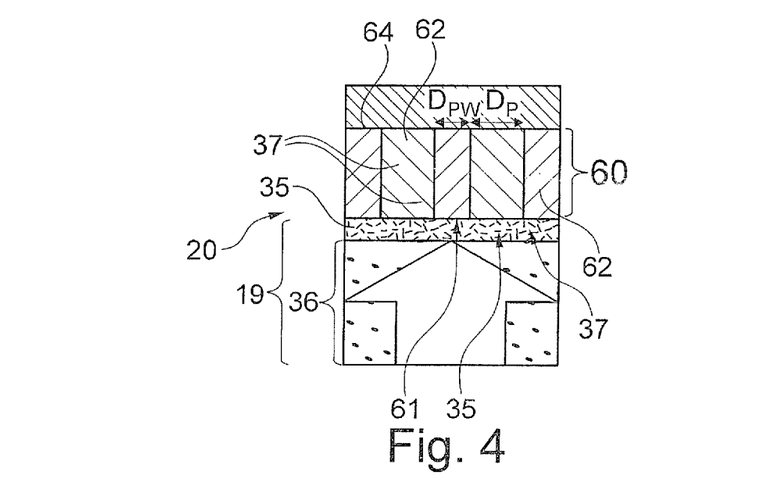
FIG. 4 is an enlarged representation of the evaporator unit of FIG. 2 in detail.
Figure 5:
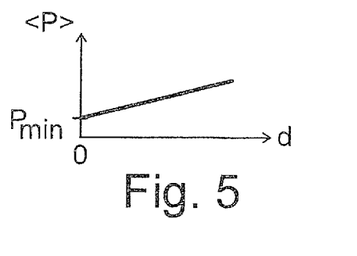
FIGS. 5 and 6 are diagrams to illustrate the functional relationship between the average pore/capillary size of the wick structure over the distance from the heating body for two different embodiments.
Figure 6:
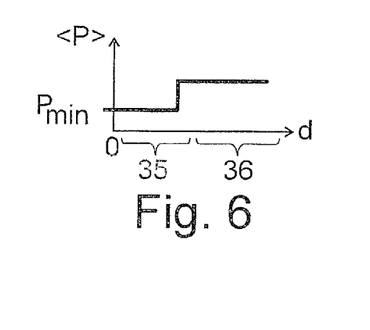

The previously described relationship between the average pore/capillary size and the distance d from the heating body 60 in the multi-layer design 35, 36 of the wick structure 19 according to FIGS. 2 and 4 is illustrated in the diagram according to FIG. 6.

In an advantageous practical embodiment, the wick layer 35 can be, for example, a fibre paper or ceramic paper layer and/or the layer 36 can be a porous ceramic.

FIG. 4 also shows that air bubbles formed in the microchannels 62 do not penetrate significantly into the wick layer 35 and thus into the wick layer, nor can they jump into bordering microchannels 62.

Of course, the wick structure 19 can have more than two wick layers 35, 36, . . . . Even in the case of more than two wick layers 35, 36, . . . , the average pore/capillary size advantageously becomes monotonically (i.e. from wick layer to wick layer) smaller and/or remains the same as the distance from the heating body 60 decreases, and therefore does not increase in any case.

In the embodiment according to FIG. 3, the wick structure 19 consists of only one layer, the average pore/capillary size of which decreases monotonically as the distance d from the heating body 60 decreases. The relationship between the average pore/capillary size and the distance d from the heating body 60 in the single-layer embodiment according to FIG. 3 is illustrated in the diagram according to FIG. 5.

In all embodiments, the desired pore/capillary size gradient can be optimally set and the flow of liquid to the heating body 60 can be slowed down and made uniform.

The described reduction in the average pore/capillary size in the wick structure 19 as the distance from the heating body 60 decreases applies in the direction perpendicular to the inlet side 61 of the heating body, i.e. perpendicular to the contact face between the heating body 60 and the wick structure 19, or parallel to the course of the microchannels 62. In contrast, within a view with the same distance d from the heating body 60, the average pore/capillary size in the wick structure 19 is advantageously constant such that all of the microchannels 62 of the heating body 60 are uniformly supplied with liquid.

The microchannels 62 are preferably arranged with the longitudinal axis thereof transverse to the layers 19, 35, 36 or more generally to any layer sequence. In this way, optimal heat input from the heating body 60 into the microchannels 62 can be achieved.

The heating body 60 can be advantageously manufactured from parts of a wafer using thin film layer technology, which wafer has a layer thickness of preferably less than or equal to 1000 μm, more preferably 750 μm, even more preferably less than or equal to 500 μm. Surfaces of the heating body 60 can advantageously be hydrophilic. The outlet side 64 of the heating body 60 can advantageously be microstructured or have micro-grooves.

The evaporator unit 20 is set in such a manner that a quantity of liquid is added preferably in the range between 1 μl and 20 μl, more preferably between 2 μl and 10 μl, even more preferably between 3 μl and 5 μl, typically 4 μl per puff by the consumer. The evaporator unit 20 can preferably be set with regard to the liquid/vapour quantity per puff, i.e. from 1 s to 3 s per puff duration.

Advantageous embodiments of an evaporator unit 20 are shown in FIGS. 7 to 10.

Figure 7:
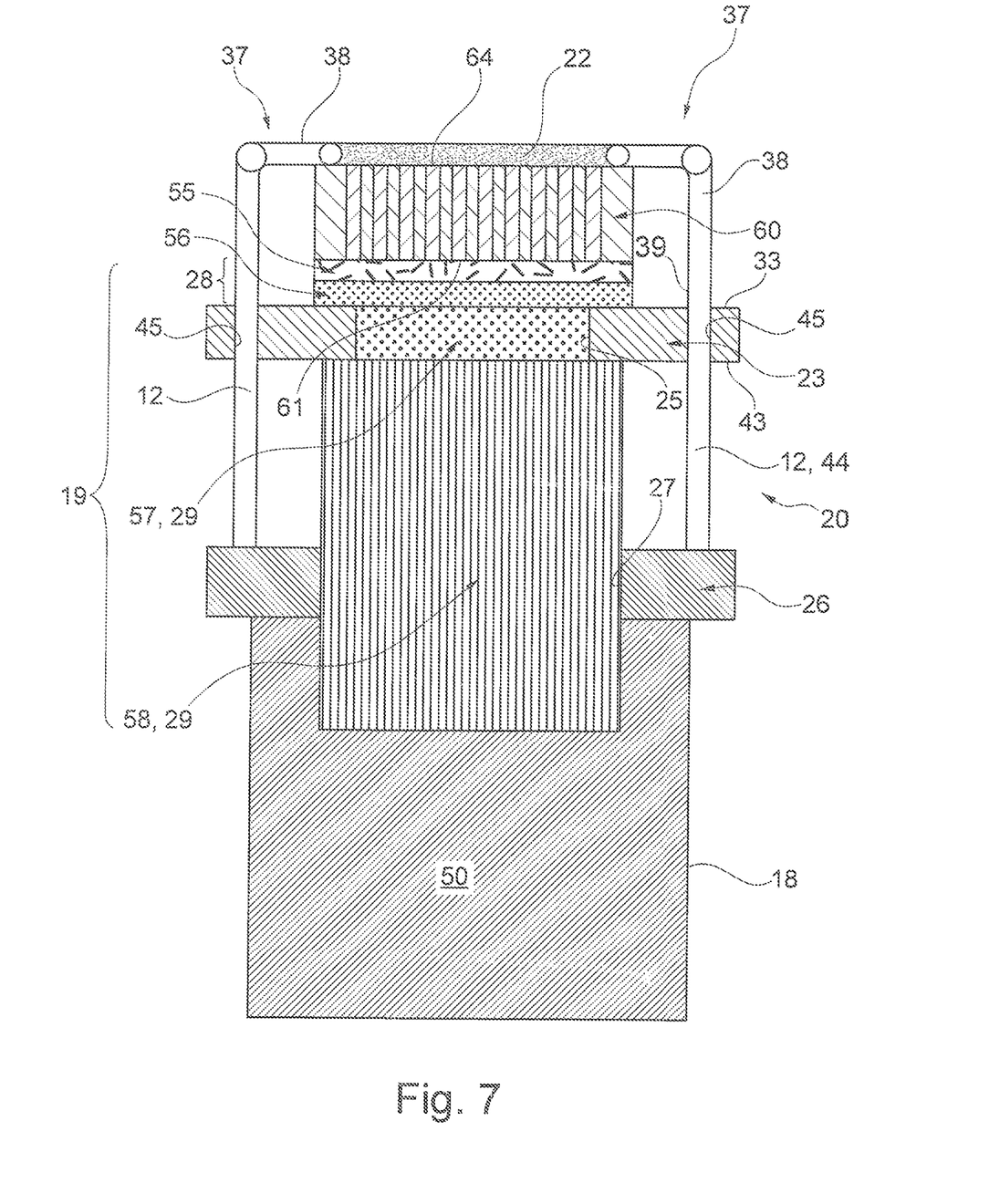
FIG. 7 is a schematic cross-sectional view of an evaporator unit in an embodiment of the invention.

In the embodiment according to FIG. 7, the wick structure 19 comprises more than two, in this case four, layers. A filter layer 55 is arranged immediately adjacently to the heating body 60, makes contact with said body over the surface, and can in particular consist of one, two or more micro-glass fibre layers. A fibrous paper layer 56 can be arranged adjacently thereto so as to be surface-to-surface. Wick layers 57, 58 are advantageously provided adjacently thereto so as to be surface-to-surface, for example a ceramic wick layer 57 and an oil lamp wick layer 58, i.e. a glass fibre wick material which is conventionally used for the wicks of oil lamps.

In the embodiment according to FIG. 7, at least the layer 55 resting flat against the heating body 60 advantageously fulfils the previously explained conditions for the pore/capillary size Dw Dp, Dpw. The layer 57 and/or the layer 58 can advantageously also meet these conditions. The capillary forces for the capillary transfer of liquid from the liquid store 18 to the heating body 60 can be provided predominantly or completely by the wick layers 57, 58. It is generally not necessary that all layers of the wick structure 19 provide capillary forces for the capillary transfer of the liquid. It may also be sufficient that only one layer of the wick structure 19 provides capillary forces for the capillary transfer of the liquid.

The evaporator unit 20 advantageously has an in particular panel-like support 23 for holding the heating body 60 and/or the wick structure 19, as shown in FIGS. 7 to 10. The support 23 can consist of a suitable material, for example ceramic, glass and/or plastics material, including fibre-reinforced plastics material, for example printed circuit board material, and has a through-opening 25, through which the wick structure 19 extends and in which the wick structure 19 is held.

The thickness D of the support 23 (see FIG. 10) is preferably in the range between 0.5 mm to 4 mm, more preferably in the range between 1 mm and 3 mm, even more preferably in the range between 1 mm and 2 mm and can be, for example, 1.6 mm or 2 mm. The thickness of a wick layer 57 arranged in the through-opening 25 of the support 23 can be adapted to or can correspond to the thickness of the support 23 and therefore also be 1.6 mm or 2 mm, for example.

The through-opening 25 is advantageously circular, which is easy to manufacture. The diameter d, or possibly the average diameter, of the through-opening 25 (see FIG. 10) is preferably in the range between 0.5 mm and 4 mm, preferably in the range between 1 mm and 3 mm, more preferably in the range between 1.5 mm and 2.5 mm and is, for example, 2 mm.

Figure 10:
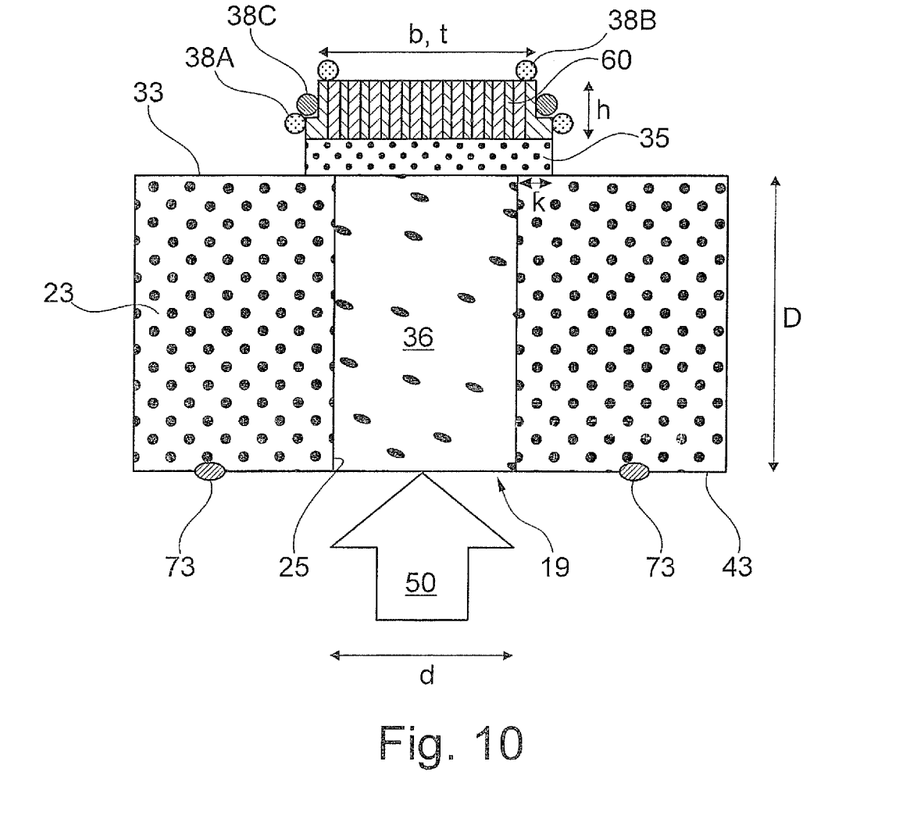
FIG. 10 is a cross-sectional view of an evaporator unit in further embodiments of the invention.

The diameter d of the through-opening 25 is less than or equal to, advantageously less than the width b of the heating body 60, see FIG. 10. The volume of the through-opening 25, or the wick volume in the through-opening 25, is advantageously in the range between 1 $mm^3$ and 8 $mm^3$, preferably in the range between 2 $mm^3$ and 6.5 $mm^3$, more preferably in the range between 2.5 $mm^3$ and 5 $mm^3$.

In the free, pre-assembled state, the wick structure 19 can have an oversize, i.e. a larger diameter than the through-opening 25, in order to generate additional holding forces of the shaft 29 in the through-opening 25.

The diameter t of the wick layer 35 (see FIG. 10) is advantageously greater than the diameter d of the through-opening 25. The wick layer 35 preferably protrudes around the entire periphery thereof over the through-opening 25 with a protrusion k. Due to the protrusion of the wick layer 35 on all sides over the through-opening 25, when the heating body 60 is clamped onto the support 23, the wick layer 35, and thus the entire wick structure 19, is securely held in the evaporator unit 20.

Figure 8:
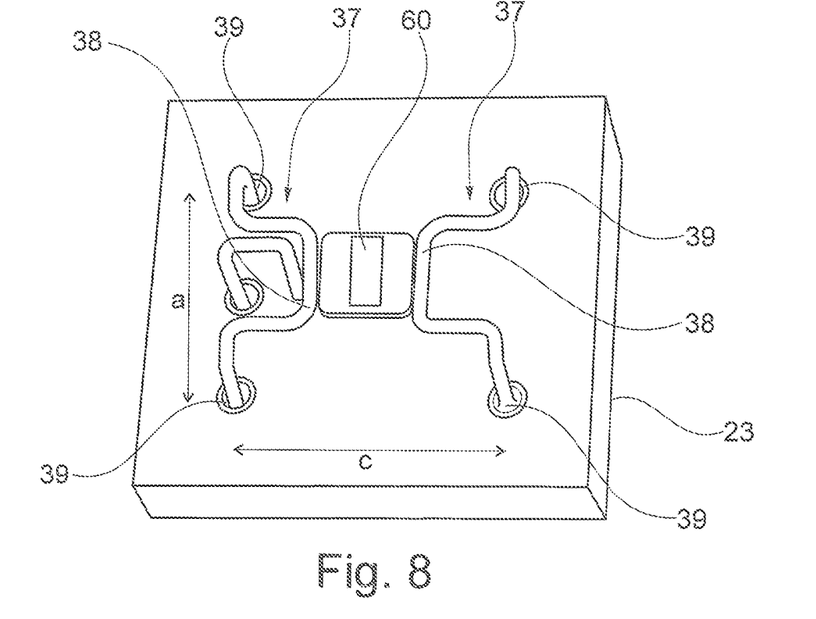
FIGS. 8 and 9 are plan views of the support of an evaporator unit from the side of the heating body (FIG. 4) and from the opposite side of the liquid supply (FIG. 5)
Figure 9:
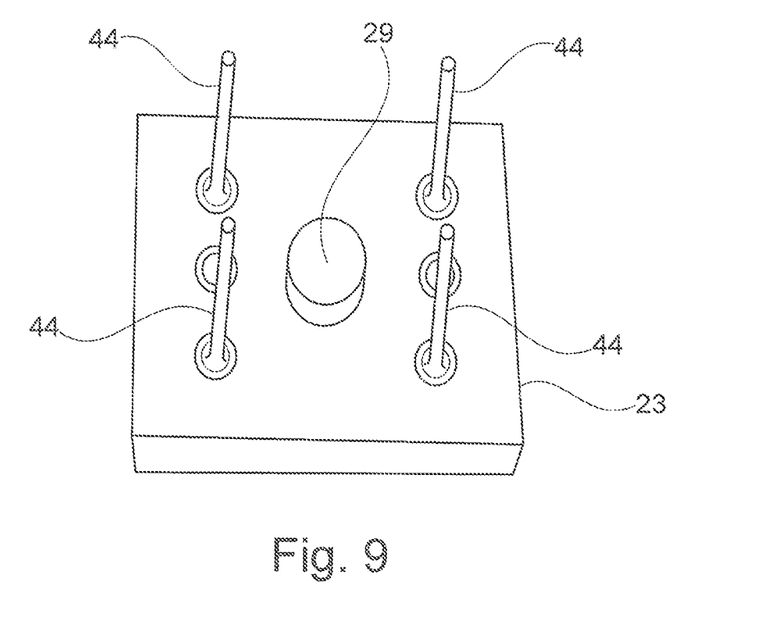

The heating body 60 is clamped on the support 23 by means of at least two clamping elements 37, see in particular FIG. 8, which engage the heating body 60 on opposite sides thereof. Each clamping element 37 advantageously has a clamping bracket 38 which is resiliently fastened to the support 23 at two mutually spaced fastening points 39 and generates a preload, by means of which the heating body 60 and the plate 28 are clamped on the support 23 and thus held securely.

The distance a between the two fastening points 39 of a clamping bracket 38 is preferably in the range between 4 mm and 10 mm, more preferably in the range between 5 mm and 8 mm and is, for example, 6 mm. The distance c between the fastening points 39 of two clamping brackets 39 is preferably in the range between 5 mm and 12 mm, more preferably in the range between 6 mm and 10 mm and is, for example, 8 mm. The dimensions of the rectangular support 23, for example, are preferably in the range between 6 mm and 20 mm, more preferably in the range between 8 mm and 17 mm and even more preferably in the range between 10 mm and 14 mm.

The clamping elements 37 are used particularly advantageously at the same time as electrodes for contacting the heating body 60 and supplying said body with heating current. For this purpose, the clamping elements 37 or the clamping brackets 38 advantageously consist of an electrically conductive material; for example this can be metal wire, for example brass wire. Due to the line contacting between the clamping bracket 38 and the heating body 60, there is an excellent electrical connection between the clamping element 37 and the heating body 60, while at the same time having ideal thermal decoupling between the clamping element 37 and the heating body 60 due to the lack of face-to-face contact. Heat dissipation from the heating body 60 into the clamping element 37 is therefore low; the clamping brackets 38, which can be used as electrodes remain significantly cooler than the heating body 60. Diode effects are avoided and purely ohmic charge carrier transport is made possible.

The clamping bracket 38 can clamp the heating body 60 laterally to and in parallel with the outlet side 64 (position 38A in FIG. 10) and/or vertically onto the outlet side 64 (position 38B in FIG. 10) and/or, in a corner groove having an intermediate angle, for example between 30° and 60°, both laterally and vertically onto the outlet side 64 (position 38C in FIG. 10). The latter possibility involves two contact lines between the clamping bracket in position 38C and the heating body 60, which further improves the electrical contacting. A clamping element 37 can also have more than one clamping bracket 38, in particular any two or all three of the clamping brackets in positions 38A, 38B, and 38C.

The clamping elements 37 are advantageously connected to a printed circuit board 26 (PCB) provided in the consumption unit or cartridge 17 by means of electrical lines 12 in order to establish the electrical connection to the electronic control device 15 and to the energy source for the supply of current to the heating body 60. Electronic components of the consumption unit or cartridge 17 are advantageously arranged on the printed circuit board 26.

In the embodiment according to FIG. 7, the printed circuit board 26 is a separate part and is spaced apart from the support 23 on the side 43 thereof facing away from the heating body 60. The printed circuit board 26 has a through-opening 27, through which the wick structure 19 extends and in which the wick structure 19 is held. The electrical lines 12 in this case comprise, for example, four metal pins 44, which are connected, on the side 33 of the support 23 in the fastening points 39, to the clamping elements 37 and in each case extend through a through-hole 45 through the support 23 and then bridge the distance between the support 23 and the printed circuit board 26 on the side 43 facing away.

In another embodiment, the support 23 can form the printed circuit board 26. The electrical lines 12 can then be omitted. It is also possible that the evaporator unit 20 itself does not comprise a printed circuit board, but rather the clamping brackets 38 are connected to a printed circuit board arranged for instance in the base part 16, for example via flexible insulated lines 12, or in another suitable manner.

A sealing element 73, for example a sealing ring, can be arranged on the underside 43 of the support 23 in order to seal the support 23 against a housing of the liquid store 18, or another component arranged under the support 23, see FIG. 10.

The course of the evaporation process is explained below.

In an initial state, the heating voltage source 71 is switched off for the heating process.

To evaporate liquid 50, the heating voltage source 71 for the heating body 60 is activated. The voltage Uh is set in such a manner that the evaporation temperature in the heating body 60 and therefore in the microchannels 62 is adapted to the individual evaporation behaviour of the liquid mixture used. This prevents the danger of local overheating and thereby the formation of harmful substances.

As soon as a quantity of liquid that corresponds to or is related to the volume of the microchannels 62 has evaporated, the heating voltage source 71 is deactivated. Since the liquid properties and quantity are advantageously known precisely and the heating body 60 has a measurable temperature-dependent resistance, this point in time can be very precisely determined or controlled. The energy consumption of the evaporator unit 20 can therefore be reduced in comparison with known devices, since the required evaporation energy can be dosed and thereby introduced more precisely.

After the heating process is complete, the microchannels 62 are largely or completely emptied. The heating voltage source 71 is then kept switched off until the microchannels 62 are replenished by subsequently transferring liquid through the wick structure 19. When this happens, the next heating cycle can be started by switching on the heating voltage source 71.

The activation frequency of the heating body 60 generated by the heating voltage source 71 is generally advantageous in the range of from 1 Hz to 50 kHz, preferably in the range of from 30 Hz to 30 kHz, and even more advantageously in the range of from 100 Hz to 25 kHz.

The frequency and the duty cycle of the heating voltage Uh for the heating body 60 are advantageously adapted to the natural vibration or natural frequency of the bubble vibrations during the bubble boiling. The period duration 1/f of the heating voltage can therefore advantageously be in the range between 5 ms and 50 ms, more advantageously between 10 ms and 40 ms, even more advantageously between 15 ms and 30 ms and can be, for example, 20 ms. Depending on the composition of the evaporated liquid, frequencies other than those specified can be optimally adapted to the natural vibration or natural frequency of the bubble vibrations.

Furthermore, it has been found that the maximum heating current generated by the heating voltage Uh should preferably not exceed 7 A, more preferably not exceed 6.5 A, even more preferably not exceed 6 A and should optimally be in the range between 4 A and 6 A in order to ensure concentrated vapour while avoiding overheating.

The transfer rate of the wick structure 19 is in turn optimally adapted to the evaporation rate of the heating body 60, meaning that sufficient liquid can be subsequently transferred at any time and the region in front of the heating body 60 is prevented from running dry.

The evaporator unit 20 is preferably produced on the basis of MEMS technology, in particular from silicon, and is therefore advantageously a micro-electromechanical system.

According to the above, a layered structure consisting of a Si-based heating body 60, which is advantageously planar at least on the inlet side 61, and of one or more capillary structures 19 located underneath said body and having advantageously different pore sizes is proposed. The wick structure 19 arranged directly on the inlet side 61 of the heating body 60 prevents the formation of bubbles on the inlet side 61 of the heating body 60, since gas bubbles inhibit a further transfer effect and at the same time lead to (local) overheating of the heating body 60 due to lack of cooling by liquid flowing in.

Embodiments

Embodiment 1. Evaporator unit for an inhaler, in particular for an electronic cigarette product, comprising an electrically operable, in particular planar, heating body (60) which has an inlet side (61) and an outlet side (64), and a plurality of microchannels (62) which each extend from the inlet side (61) to the outlet side (64) through the heating body (60), the heating body (60) being designed to evaporate, by applying a heating voltage, liquid transferred through the microchannels (62), characterised in that a porous and/or capillary wick structure (19) is arranged on the inlet side (61) of the heating body (60), which structure rests flat against and in contact with the heating body (60) and covers all of the microchannels (62) on the inlet side (61).

Embodiment 2. Evaporator unit according to embodiment 1, characterised in that the average pore/capillary size of pores or capillaries in the wick structure (19) in the contact region with the heating body (60) is smaller, preferably at least one order of magnitude smaller, than the smallest distance of two microchannels (62) from one another.

Embodiment 3. Evaporator unit according to either embodiment 1 or embodiment 2, characterised in that the average pore/capillary size of pores in the wick structure (19) in the contact region with the heating body (60) is smaller, preferably at least one order of magnitude smaller, than the smallest inside diameter of the microchannels (62).

Embodiment 4. Evaporator unit according to any of the preceding embodiments, characterised in that the average pore/capillary size in the wick structure (19) changes in particular monotonically as the distance from the heating body (60) decreases.

Embodiment 5. Evaporator unit according to embodiment 4, characterised in that the average pore/capillary size in the wick structure (19) reduces in particular monotonically as the distance from the heating body (60) decreases.

Embodiment 6. Evaporator unit according to either embodiment 4 or embodiment 5, characterised in that the wick structure (19) has one or more porous and/or capillary layers, the pores or capillaries of which each have a constant average pore/capillary size.

Embodiment 7. Evaporator unit according to either embodiment 4 or embodiment 5, characterised in that the wick structure (19) comprises a porous and/or capillary layer having a gradual change, in particular a decrease in the pore/capillary size in the direction towards the heating body.

Embodiment 8. Evaporator unit according to any of the preceding embodiments, characterised in that the transfer rate of the wick structure (19) is at least as great as the maximum evaporation rate of the heating body (60).

Embodiment 9. Evaporator unit according to any of the preceding embodiments, characterised in that the wick structure consists of one or more from the group of the materials cotton, cellulose, acetate, glass fibre fabric, glass fibre ceramic, sintered ceramic, ceramic paper, aluminosilicate paper, metal foam, metal sponge, another heat-resistant, porous and/or capillary material having a suitable transfer rate, or a combination of two or more of the aforementioned materials.

Embodiment 10. Evaporator unit according to any of the preceding embodiments, characterised in that the wick structure (19) has a filter layer (55), in particular made of micro-glass fibre.

Embodiment 11. Evaporator unit according to any of the preceding embodiments, characterised in that the wick structure (19) has a fibre paper layer (56).

Embodiment 12. Evaporator unit according to any of the preceding embodiments, characterised in that the wick structure (19) has a ceramic wick layer (57).

Embodiment 13. Evaporator unit according to any of the preceding claims, characterised in that the wick structure (19) has an oil lamp wick layer (58).

Embodiment 14. Evaporator unit according to any of the preceding embodiments, characterised in that the evaporator unit has a substrate (23) comprising a through-opening (25) for holding the heating body (19) and/or the wick structure (19).

Embodiment 15. Evaporator unit according to any of the preceding embodiments, characterised in that the evaporator unit has a holding element (26), in particular in the form of a printed circuit board, comprising a through-opening (27) for holding the wick structure (19).

Embodiment 16. Evaporator unit according to any of the preceding embodiments, characterised in that the frequency and/or duty cycle of a heating voltage Uh for the heating body (60) is adapted to the natural vibration and/or natural frequency of vibrations of gas bubbles formed in the microchannels (62).

Embodiment 17. Evaporator unit according to embodiment 16, characterised in that the frequency and/or duty cycle of the heating voltage Uh is optimally selected depending on the mixing ratio of the liquid to be evaporated.

Embodiment 18. Evaporator unit according to either embodiment 16 or 17, characterised in that the frequency of the heating voltage Uh is in the range between 20 Hz and 200 Hz.

Embodiment 19. Evaporator unit according to any of the preceding embodiments, characterised in that the maximum heating current generated by a heating voltage Uh for the heating body (60) is not more than 7 A.

Embodiment 20. Evaporator unit according to any of the preceding embodiments, characterised in that the evaporator unit (20) has at least one clamping element (37) which generates a preload and is arranged and designed to clamp the heating body (60) onto the support (23).

Embodiment 21. Evaporator unit according to embodiment 20, characterised in that at least two clamping elements (37) are provided on opposite sides of the heating body (60).

Embodiment 22. Evaporator unit according to either embodiment 20 or embodiment 21, characterised in that the at least one clamping element (37) has a clamping bracket (38) which makes linear contact with the heating body (60).

Embodiment 23. Evaporator unit according to any of embodiments 20 to 22, characterised in that the at least one clamping element (37) clamps the heating body (60) laterally to and in parallel with the outlet side and/or vertically onto the outlet side (64) and/or in a corner groove of the support (23).

Embodiment 24. Evaporator unit according to any of embodiments 20 to 23, characterised in that the at least one clamping element (37) is used as an electrode for electrically contacting and supplying power to the heating body (60).

Embodiment 25. Evaporator unit according to embodiment 24, characterised in that at least one conductor (12) extending through a hole (45) in the support (23) is provided for contacting the clamping element (37).

Embodiment 26. Evaporator unit according to embodiment 25, characterised in that the at least one conductor (12) contacts a printed circuit board (26) which is arranged on the side of the support (23) and spaced apart from the support (23) facing away from the heating body (60).

Embodiment 27. Evaporator unit according to any of the preceding embodiments, characterised in that the support (23) is in the form of a printed circuit board.

The invention claimed is:

1. An evaporator unit for an inhaler, comprising:
an electrically operable heating body that has an inlet side, and an outlet side, and a plurality of microchannels that each extend from the inlet side to the outlet side through the electrically operable heating body,
wherein the electrically operable heating body is configured to evaporate, by applying a heating voltage, liquid transferred through the plurality of microchannels,
wherein a porous and/or capillary wick structure is arranged on the inlet side of the electrically operable heating body, wherein the porous and/or capillary wick structure rests flat against and in contact with the electrically operable heating body and covers all of the microchannels on the inlet side.

2. The evaporator unit according to claim 1, wherein an average pore/capillary size of pores or capillaries in the porous and/or capillary wick structure in a contact region with the electrically operable heating body is smaller than a smallest distance of any two microchannels of the plurality of microchannels from one another.

3. The evaporator unit according to claim 1, wherein an average pore/capillary size of pores in the porous and/or capillary wick structure in the contact region with the electrically operable heating body is smaller than a smallest inside diameter of the microchannels of the plurality of microchannels.

4. The evaporator unit according to claim 1, wherein an average pore/capillary size in the porous and/or capillary wick structure changes monotonically as a distance from the electrically operable heating body decreases.

5. The evaporator unit according to claim 4, wherein the average pore/capillary size in the porous and/or capillary wick structure reduces monotonically as the distance from the electrically operable heating body decreases.

6. The evaporator unit according to claim 1, wherein the porous and/or capillary wick structure has one or more porous and/or capillary layers, pores or capillaries of which each have a constant average pore/capillary size.

7. The evaporator unit according to claim 1, wherein the porous and/or capillary wick structure comprises a porous and/or capillary layer having a gradual decrease in the pore/capillary size in the direction towards the electrically operable heating body.

8. The evaporator unit according to claim 1, wherein a transfer rate of the porous and/or capillary wick structure is at least as great as the maximum evaporation rate of the electrically operable heating body.

9. The evaporator unit according to claim 1, wherein the porous and/or capillary wick structure comprises one or more materials from the following group of materials: cotton, cellulose, acetate, glass fibre fabric, glass fibre ceramic, sintered ceramic, ceramic paper, aluminosilicate paper, metal foam, metal sponge, another heat-resistant, porous and/or capillary material having a suitable transfer rate, and a combination of two or more materials of the aforementioned materials.

10. The evaporator unit according to claim 1, wherein the porous and/or capillary wick structure has a filter layer, made of micro-glass fibre.

11. The evaporator unit according to claim 1, wherein the porous and/or capillary wick structure has a fibre paper layer.

12. The evaporator unit according to claim 1, wherein the porous and/or capillary wick structure has a ceramic wick layer.

13. The evaporator unit according to claim 1, wherein the porous and/or capillary wick structure has an oil lamp wick layer.

14. The evaporator unit according to claim 1, wherein the evaporator unit has a substrate comprising a through-opening for holding the electrically operable heating body and/or the porous and/or capillary wick structure.

15. The evaporator unit according to claim 1, further comprising: a holding element, in the form of a printed circuit board, wherein the holding element comprises a through-opening for holding the porous and/or capillary wick structure.

16. The evaporator unit according to claim 1, wherein a frequency and/or duty cycle of a heating voltage Uh for the electrically operable heating body is adapted to a natural vibration and/or natural frequency of vibrations of gas bubbles formed in the plurality of microchannel s.

17. The evaporator unit according to claim 16, wherein the frequency and/or duty cycle of the heating voltage Uh is selected depending on a mixing ratio of the liquid to be evaporated.

18. The evaporator unit according to claim 1, wherein a frequency of the heating voltage Uh is in a range between 20 Hz and 200 Hz.

19. The evaporator unit according to claim 1, wherein a maximum heating current generated by a heating voltage Uh for the electrically operable heating body is not more than 7 A.

20. The evaporator unit according to claim 1, further comprising:
    at least one clamping element that generates a preload and is arranged and configured to clamp the electrically operable heating body onto a support.

21. The evaporator unit according to claim 20, wherein at least two clamping elements of the at least one clamping element are provided on opposite sides of the electrically operable heating body.

22. The evaporator unit according to claim 20, wherein the at least one clamping element has a clamping bracket which makes linear contact with the electrically operable heating body.

23. The evaporator unit according to claim 20, wherein the at least one clamping element clamps the electrically operable heating body laterally to and in parallel with the outlet side and/or vertically onto the outlet side and/or in a corner groove of the support.

24. The evaporator unit according to claim 20, wherein the at least one clamping element is used as an electrode for electrically contacting and supplying power to the electrically operable heating body.

25. The evaporator unit according to claim 24, wherein at least one conductor extending through a hole in the support is provided for contacting the at least one clamping element.

26. The evaporator unit according to claim 25, wherein the at least one conductor contacts a printed circuit board which is arranged on a side of the support and spaced apart from the support facing away from the electrically operable heating body.

27. The evaporator unit according to claim 20, wherein the support is in the form of a printed circuit board.

* * * * *